(12) United States Patent
Stark et al.

(10) Patent No.: US 8,373,015 B2
(45) Date of Patent: Feb. 12, 2013

(54) PRODUCTION OF SATURATED C2 TO C5 HYDROCARBONS

(75) Inventors: Jan Wendelin Stark, Zürich (CH); Neil Osterwalder, Fehraltorf (CH)

(73) Assignee: ETH Zürich, Zürich (CH)

( * ) Notice: Subject to any disclaimer, the term of this patent is extended or adjusted under 35 U.S.C. 154(b) by 818 days.

(21) Appl. No.: 12/294,168

(22) PCT Filed: Mar. 19, 2007

(86) PCT No.: PCT/CH2007/000154
§ 371 (c)(1),
(2), (4) Date: Jun. 17, 2009

(87) PCT Pub. No.: WO2007/107031
PCT Pub. Date: Sep. 27, 2007

(65) Prior Publication Data
US 2009/0306443 A1  Dec. 10, 2009

Related U.S. Application Data

(60) Provisional application No. 60/787,897, filed on Mar. 31, 2006.

(30) Foreign Application Priority Data

Mar. 23, 2006  (EP) ..................................... 06005927

(51) Int. Cl.
*C07C 1/30* (2006.01)
(52) U.S. Cl. ........ 585/733; 585/301; 585/302; 585/314; 585/315; 585/316; 585/950
(58) Field of Classification Search .................. 585/700, 585/708, 733, 275, 264, 310, 311, 312, 313, 585/314, 315, 316, 301, 302
See application file for complete search history.

(56) References Cited

U.S. PATENT DOCUMENTS 2,434,289 A * 1/1948 Schmerling ................... 585/317
3,525,699 A   8/1970 Koppel et al.

(Continued)

FOREIGN PATENT DOCUMENTS

FR   2 300 749   2/1975
FR   2 330 663   11/1976

(Continued)

OTHER PUBLICATIONS

Woodcock, et al., "Natural Gas" in Kirk-Othmer Encyclopedia of Chemical Technology, John Wiley & Sons, 2001, published on-line Jun. 18, 2004.*

(Continued)

*Primary Examiner* — In Suk Bullock
*Assistant Examiner* — Bradley Etherton
(74) *Attorney, Agent, or Firm* — Marshall, Gerstein & Borun LLP (57) ABSTRACT

Catalytic methods for the production of saturated hydrocarbons with 2 to 5 carbon atoms per molecule by conversion of small hydrocarbon halides and/or hydrogenation of carbonaceous material are disclosed that result in high yield of saturated C2 to C5 hydrocarbons at reduced corrosion of the reactors and in good lifetime of the catalyst. The methods are performed in the presence of a Lewis acid comprising catalyst and in the absence of oxygen or oxygen containing compounds, whereby an upper limit of at most 50 parts per million mass of oxygen or oxygen containing compounds can be tolerated.

18 Claims, 5 Drawing Sheets

U.S. PATENT DOCUMENTS

| | | | |
|---|---|---|---|
| 3,578,725 A | 5/1971 | Jost | |
| 4,120,912 A * | 10/1978 | Hulme | 585/374 |
| 4,373,109 A * | 2/1983 | Olah | 585/640 |
| 4,465,893 A * | 8/1984 | Olah | 585/709 |
| 4,795,843 A * | 1/1989 | Imai et al. | 585/408 |
| 5,001,293 A * | 3/1991 | Nubel et al. | 585/408 |
| 5,171,393 A | 12/1992 | Moffat | |
| 5,276,240 A * | 1/1994 | Timmons et al. | 585/642 |
| 6,632,765 B1 * | 10/2003 | Chen | 502/53 |
| 2005/0038310 A1 | 2/2005 | Lorkovic et al. | |
| 2005/0171393 A1 * | 8/2005 | Lorkovic | 585/357 |
| 2005/0234277 A1 * | 10/2005 | Waycuilis | 585/310 |
| 2007/0238909 A1 * | 10/2007 | Gadewar et al. | 585/16 |

FOREIGN PATENT DOCUMENTS

| | | |
|---|---|---|
| GB | 1 212 446 | 10/1968 |
| GB | 1 392 197 | 4/1975 |
| WO | WO 2005/104689 | 11/2005 |

OTHER PUBLICATIONS

Olah, et al., "Friedel-Crafts Reactions" in Kirk-Othmer Encyclopedia of Chemical Technology, John Wiley & Sons, 2001, published on-line Jun. 18, 2004.*

Sokol, et al., "Computational Investigation into the Origins of Lewis Acidity in Zeolites," Adv. Mater. 2000, 12, No. 23, Dec. 1, 2000, 1801-1805.

International Search Report in corresponding PCT/CH2007/000154 dated Aug. 3, 2007.

International Preliminary Report on Patentability for corresponding PCT/CH2007/000154, dated Sep. 23, 2008.

Written Opinion for corresponding PCT/CH2007/000154, dated Sep. 23, 2008.

* cited by examiner

PRODUCTION OF SATURATED C2 TO C5 HYDROCARBONS

CROSS REFERENCES TO RELATED APPLICATIONS

This application claims the priority of European patent application 06 005 927.6, filed Mar. 23, 2006 and of U.S. provisional application 60/787,897, filed Mar. 31, 2006, the disclosures of which are incorporated herein by reference in their entirety.

TECHNICAL FIELD

The present invention concerns a process for the production of saturated C2 to C5 hydrocarbons using methane or methane rich or carbon rich non-volatile starting materials, especially a method including conversion of halogenated, in particular bromated, small hydrocarbons.

BACKGROUND ART

General background. The intensive efforts by numerous research teams over the last 60 years have resulted in numerous processes and inventions on how to convert methane into higher hydrocarbons or other industrially useful compounds. A series of authors previously succeeded in discovering and clearly identifying a range of efficient and economical chemical reaction schemes for converting methane into higher alkanes/alkenes. An overview of these different approaches to convert methane into higher value products are given in the recently published patent applications WO 2004/041399, US 2005/0171393 or by Degirmenci et al., 2005 and shall not be reproduced here. Unfortunately, no such proposed process is readily applied at a large scale since they either involve the use of expensive reagents or excessive amounts of energy, or they are very inefficient.

Halogen routes to methane conversion. First attempts to convert methyl chloride into ethylene or propylene and other products on zeolite catalysts date back to U.S. Pat. No. 4,769, 504, Lersch and Bandermann, 1991, White, et al., 1992, Murry, et al., 1994, and Sun, Yao et al., 1993, who used ZSM-5 type oxide based catalysts. U.S. Pat. No. 5,001,293 and U.S. Pat. No. 5,087,786 used a copper aluminium borate to manufacture lower alkanes. Investigations on the Lewis acidity in zeolites have been published by Sokol et al., 2000.

Particularly in the last few years, halides have been suggested as intermediates in the conversion of methane to useful products. As a consequence, various patents and a series of publications were made for the halogenation of methane to methyl chloride, methyl fluoride, methyl bromide or other methane derivatives containing halogen atoms as disclosed in U.S. Pat. No. 3,979,470, U.S. Pat. No. 4,523,040, U.S. Pat. No. 4,804,797, U.S. Pat. No. 6,452,058 and WO 2005/104689. These patent applications and patents were all motivated by the discoveries of Olah et al., 1973 in U.S. Pat. No. 4,523,040 who found excellent selectivities to mono-halogenated methanes in the eighties during the Lewis acid assisted chlorination or bromination of hydrocarbons, especially methane.

Other approaches involve the use of a metal halogenide as an oxidant for methane. The published US patent application no. 2004/0006246 A1 discloses a process wherein a reactant comprising an alkane, an alkene or an aromatic reacts with a metal halide to produce the halide of the reactant and reduced metal. The reduced metal is oxidized with air or oxygen to form the corresponding metal oxide. This metal oxide is then reacted with the halide of the reactant to form the alcohol and/or the ether corresponding to the original alkane, alkene or aromatic and the original metal halide, which is recycled. This process offers a readily accessible source of methylbromide, amongst others. The later document, WO2005/019143 A1, further claims processes for synthesizing olefins, alcohols, ethers and aldehydes, which involve the use of solid phase catalysts/reactants in addition to the metal oxides and metal halides. In addition it comprises techniques for improving the selectivity of these reactions.

A modification of the above process is described in a series of patents and patent applications: U.S. Pat. No. 6,462,243, EP 1 435 349 A2, U.S. Pat. No. 6,472,572 B1 and U.S. Pat. No. 6,486,369 B1 that disclose another process for manufacturing alcohols, ethers and olefins from alkanes. In a first step an alkane and bromine are mixed in a reactor to form alkyl bromide and hydrogen bromide. The alkyl bromide and the hydrogen bromide are directed into contact with a metal oxide to form an alcohol and/or an ether or an olefin and metal bromide. The metal bromide is oxidized to form original metal oxide and bromine. Both are recycled.

Similarly, WO 02/094751 discloses an oxidative halogenation process involving a reactant hydrocarbon selected from methane, a halogenated $C_1$ hydrocarbon, or a mixture thereof with a source of halogen and a source of oxygen in the presence of a rare earth halide or a rare earth oxyhalide catalyst, so as to form a halogenated C1 hydrocarbon. This product can be condensed catalytically as disclosed in U.S. Pat. No. 5,397,560 to from light olefins, such as ethylene, propylene, butenes, and higher hydrocarbons, including C5+ gasolines. As catalysts, various zeolithes of the ZSM structure code are mentioned. The reaction temperature is typically greater than 250° C. A very interesting approach is offered by the U.S. Pat. No. 4,973,776 by Allenger and Pandey: They describe the conversion of natural gas or methane and acetylene on solid superacids comprising a binary metal fluoride (e.g. $TaF_5$—$AlF_3$) to isobutene and subsequent conversion to gasoline-range hydrocarbons in the presence of a silicalite zeolite catalyst. Yilmaz et al., 2005 and Zhou, Xiao-Ping et al., 2003 and U.S. Pat. No. 6,472,572 B1 and U.S. Pat. No. 6,486,368 B1 found, amongst others, a process for the conversion of ethane to ethylene, ethanol, diethyl ether and other products over oxide catalysts. Similarly, Lorkovic et al., 2004 (2 papers), Noronha et al., 2005 and Sun, Shouli et al., 2004, US 2004/0006246 A1, WO 86/04577 and U.S. Pat. No. 6,462, 243 B1 describe bromine using, oxide mediated methane conversions.

WO 2004/041399 A2 describes an anhydrous sulfur based approach to methane activation. WO 2004/041399 details processes for the conversion of methane to methanol and lists anhydrous conditions as advantageous but only deals with oxygen containing products and intermediates.

Now, in order to better understand the background of the invention, it is useful to compare the out-lined existing processes and gather their characteristics: All processes involving halogens as reagents or adjuvants during the conversion of methane into useful products are confronted with the problem of converting the such generated halogenated methane into useful products. All processes for the conversion of methane inherently require the presence of carbon, hydrogen and at least one halogen, most frequently chlorine or bromine derivatives. Furthermore, all processes involve the formation of the corresponding H-Halide compounds at one step of the process. Such HCl or HBr are then generally recycled through oxidation, optionally via a metal salt intermediate. Catalysts or intermediate salts in all here described processes contain oxygen or oxides at least in one part of the process. The specific problems occurring due to the presence of H-Hal compounds and oxygen containing compounds including water, oxides, and especially zeolites, e.g. ZSM-5 like zeolites, are in more detail addressed below.

A careful analysis of why numerous processes of high attractiveness have failed commercialization in the past, reveals the dominant role of several factors that are often neglected when developing processes at a small scale:

1. Reactor stability. Attractive reactor or reaction design must enable a corrosion reduced environment to maintain operation over an extended period of time. Corrosion may come from high temperature, rapid temperature changes, aggressive chemicals, and others.
2. Catalyst stability. The active materials involved in the preparation of large-scale commodity materials of very low price and margins must be stable or recyclable over hundreds or even thousands of cycles. Therefore, such systems must be fully recycled, or they are virtually made de novo during each cycle of the process.
3. Energy requirements. In order to get a reasonable part of the methane converted into useful products, the energy requirements per cycle must inherently be low and the conversion of methane per cycle should be as high as possible, best close to 100%.

While the halogen assisted methane activation offers a most attractive route to useful products, the yet existing processes may be split in three parts:

A) Methane halogenation (formation of methyl chloride or bromide)
B) Conversion of methyl halogen derivative (e.g. conversion to C3 to C5 hydrocarbons or oxygenates)
C) Recycling of H-Halogen compounds to the halogen itself (e.g. chlorine or bromine)

Part A has been repeatedly described in the open scientific literature (e.g. Olah et al., 1985) and part C is also implemented into current industrial processes for the manufacturing of bromine. Therefore, most of today possible innovation can be made in part B, or, more specifically, in the conversion to the desired products. This is also the step where the selectivity and conversion rate of different processes decide on the overall outcome and efficiency of a process. Hence, the present invention primarily deals with an improved process of part B.

Looking at the predominant three large-scale-production problems (1 to 3, above), the use of halogenated compounds inherently addresses the question of corrosion of catalysts and reactor materials. The skilled researcher will easily remember the chemical properties of hydrochloric or hydrobromic acid which involve highly aggressive attack of most construction materials, be it metals or oxides. The problem of handling large volumes of HCl, HBr and other halogen-hydrogen compounds is well known. Indeed, corrosion in the processes disclosed by some of the previously cited patents and publications do require sophisticated alloys even when processing small laboratory scale amounts. Other corrosion processes by using HCl and HBr are well known and attack even highly alloyed steels. Furthermore, the use of alumina silicates or other oxidic systems as catalysts suffers from equilibrium between the oxide (MOx) and the halogenide (Hal):

$$MO_x + y HHal = MO_{(x-2y)} Hal_y + y/2 H_2O \qquad \text{(eqn. 1)}$$

Unfortunately, most metal halides and oxyhalides are quite volatile. Therefore, catalysts under such conditions are suffering from a lack of long term stability. The shift of the equilibrium at lower temperatures inherently results in chemical transport of parts of the catalyst and deposition of catalyst material within other parts of the reactor. Finally, such deposits are clogging tubes and induce failure of valves or whole components while the loss of catalytic activity also affects the overall plant performance. This effect can easily be made visible e.g. by the following experiment:

A piece of quartz wool (100 mg) is placed in a quartz tube (inner diameter about 6 mm) and heated by an external furnace to temperatures in the range of 150 to 500° C. while passing a stream of methyl chloride (5 vol % in argon, 10 ml per minute) through the tube. After a few hours, solid white deposits are formed at the colder end of the tube where it leaves the hot region downstream of the quartz wool. This readily demonstrates the volatility of a normally quite resistant and inert material like quartz wool. The outlined experiment can also be made with other silica based materials and even ceramic oxides undergo partial chemical transport. Active metals are often described as suitable dopants on zeolite catalysts. But e.g. many metals described as suitable on ZSM-5 in PCT/US2005/012655, undergo chemical transport as described above. This illustrates readily and clearly that such oxidic materials are of limited applicability for the conversion of methyl chloride or methyl bromide. Still, numerous authors have claimed patents in this area and used such oxide based materials.

Several catalysts have been proposed in connection with hydrocarbon modification. U.S. Pat. No. 3,578,725 discloses an aluminum halide catalyst for isomerizing hydrocarbons and GB patent 1212446 proposes the use of a catalyst system comprising a trihalonickelate complex and a lewis acid for dimerization of olefins.

PCT/US2005/012655 also lists the advantageous use of water free feed streams during bromination of methane but only lists a suppressed formation of carbon dioxide as a motivation.

Problems arising from handling HBr are described in great detail by Smudde et al., 1995. This work clearly shows how mixtures of water vapor of as low as 1700 ppm and air-contaminated HBr are corrosive to even highly alloyed stainless steels even comprising Hastelloy C-22 or Ni-200 and EP 316L.

DISCLOSURE OF THE INVENTION

Hence, it is a general object of the invention to provide a process for the halogen assisted conversion of methane to higher hydrocarbons that is less corrosive and provides good yield and improved long-term catalyst stability. Ideally, a process of part B (see above) provides a safe, corrosion reduced, high yield conversion of a methyl halide into useful products, especially smaller hydrocarbons.

It is another object of the present invention to provide a method for regenerating carbon deposits formed in the conversion reactor and on the catalyst.

It is yet another object of the present invention to provide a method for converting non-volatile carbonaceous material into smaller hydrocarbons.

Now, in order to fulfill these and still further objects of the invention, which will become more readily apparent as the description proceeds, a strongly modified process for the conversion of methyl halides into useful products is described in the following section.

This method for the production of saturated hydrocarbons with 2 to 5 carbon atoms per molecule by conversion of small hydrocarbon halides is manifested by the features that the hydrocarbon halide is reacted over a transition metal bromide and/or a Lewis acid comprising catalyst under the exclusion of any oxygen or oxygen containing compounds exceeding a level of at most 50 parts per million mass.

To achieve the foregoing and other objects, and in accordance with the purpose of the present invention, one embodiment of the present invention is a process for converting methane and other small hydrocarbons into larger hydrocarbons.

As utilized in the following description, the term "small hydrocarbons" refers to methane, ethane and propane and includes mixtures of these hydrocarbons alone or together with ethylene and propylene. A preferred small hydrocarbon is methane or methane rich starting material. Also utilized throughout the description, the term methyl bromide denotes methyl monobromide $CH_3Br$ with at maximum content of methane dibromide $CH_2Br_2$ and tribromomethane $CHBr_3$ of 5 mol-%. Alkyl bromide refers to bromides of ethane or propane irrespectively of the degree of oxidation, e.g. it includes $C_2H_3Br$ (bromoethylene) and others.

The process comprises reacting said small hydrocarbon or methane feed with halogen (Hal) vapor, advantageously bromine vapor, to form alkyl halogenides, advantageously alkyl bromides, much preferred methyl bromide, and hydrohalogenic acid, advantageously hydrobromic acid. A suitable process performed with bromine is e.g. described by Olah et al., 1985 or based thereon. The water and oxygen free alkyl halogenide, advantageously the methyl bromide, is then pressurized over a transition metal bromide and/or Lewis acid comprising catalyst (further on also referred to as catalyst), preferably a Lewis acid with optionally other metals or metal derivatives, such as non-oxide metal salts, preferably alkali metal salts and/or earth alkaline metal salts and/or transition metal bromides while excluding the presence of even minute amounts of water vapor or the presence of any oxygen in said catalyst (e.g. the salts comprised therein) or the reactor (environment). This complete exclusion of oxygen in any form allows to keep corrosion in the reactors and catalyst materials used for this reaction to a minimum. Nevertheless it may be necessary to enhance the lifetime of the reactor by using a reactor with non-corrosive surface, such as e.g. a non-corrosive coating of e.g. noble metals, metal nitrides, tantalum etc. Materials data and tests may be found e.g. in Smudde et al., 1995 and references therein. The alkyl halogenide, in particular the methyl bromide, is then converted into product hydrocarbons, HHal and carbon that deposits within the pressurized reactor. In a second step, the product hydrocarbons and HHal are released from the reactor, separated and HHal recycled to halogen vapor. For hydrobromic acid the conversion to bromine vapor is e.g. described in GB 1,088,441, U.S. Pat. No. 2,163,877, and JP 52 095 594. Carbon and transition metal bromide and/or Lewis acid comprising catalyst, preferably a Lewis acid with optionally other metals or non-oxide metal salts, are then contacted to hydrogen under pressure which converts the carbon into a second part of product hydrocarbons. This regeneration step removes most carbon from the catalyst and directly converts such carbon into useful product hydrocarbons. Therefore, this two step process can convert one equivalent of methyl halogenide, in particular methyl bromide, almost quantitatively (e.g. high conversion process) into product hydrocarbons while minimizing the need for multiple repetition of small-conversion processes.

In another embodiment of the present invention, a process is provided for converting small hydrocarbons into product hydrocarbons where the alkyl halogenide, in particular the methyl bromide, is reacted with a suitable transition metal bromide and/or Lewis acid comprising catalyst, in particular a Lewis acid with optionally other metals or metal derivatives, such as non-oxide metal salts, preferably alkali metal salts and/or earth alkaline metal salts and/or transition metal bromides, under the addition of suitable amounts of hydrogen or other suitable reducing agents (reductants) and under the total exclusion of oxygen, water or any oxides. This modification of the process therefore combines the two separate steps of the first embodiment described before. The hydrogen pressure is chosen as to suppress the deposition of carbon while not strongly interfering with the conversion of methyl bromide.

In still another embodiment of the present invention, a process for the conversion of carbon or carbonaceous matter or non-volatile carbon rich tars, soot, bitumen or other carbon sources into product hydrocarbons is described. This process comprises the drying of such carbon and conversion with hydrogen, a transition metal bromide and/or Lewis acid comprising catalyst, in particular a Lewis acid and optionally other metals or metal derivatives, such as non-oxide metal salts, preferably alkali metal salts and/or earth alkaline metal salts and/or transition metal bromides, whilst excluding any oxygen, water or oxides in the process. Such process then delivers exclusively small hydrocarbons ranging from ethane to pentane at molar yield above 62% of converted carbon.

With regard to all these processes it has proved to be advantageous not to aim at full hydrogenation of the carbon but to work in a range of about 50 to 80% hydrogenation referred to the total carbon content.

BRIEF DESCRIPTION OF THE DRAWINGS

The invention will be better understood and objects other than those set forth above will become apparent when consideration is given to the following detailed description thereof. Such description makes reference to the annexed drawings, which are incorporated in and form a part of the specification, illustrate the embodiments of the present invention and, together with the description, serve to explain the details and principles of the invention.

In the Drawings.

MODES FOR CARRYING OUT THE INVENTION

A preferred halogenated small hydrocarbon starting material is methyl bromide. In a preferred embodiment of the process, the methyl bromide is obtained by bromination of natural gas after removal of all oxygen containing species to a level below 50 ppm (weight oxygen per weight gas in total), preferable below 5 ppm. This stays in clear contrast to PCT/US2005/012655 where up to 2 mol-% $CO_2$ are tolerated. Such low oxygen levels must be maintained to keep corrosion at a minimum. Therefore, significant efforts may be required to remove oxygen, water and oxygenated impurities from the feed gas.

Another suitable methane source is methane from the Fischer-Tropsch conversion of syngas. If such product is used as methylbromide source, a step converting the methane to methyl bromide and the conversion method of the present invention can be joined to a classical Fischer-Tropsch process such that the methane is directly converted or reacted to small saturated hydrocarbons. In addition, the high boiling or non volatile products from the Fischer-Tropsch process can be inserted in the regeneration step also forming part of the present invention.

Figure 1:
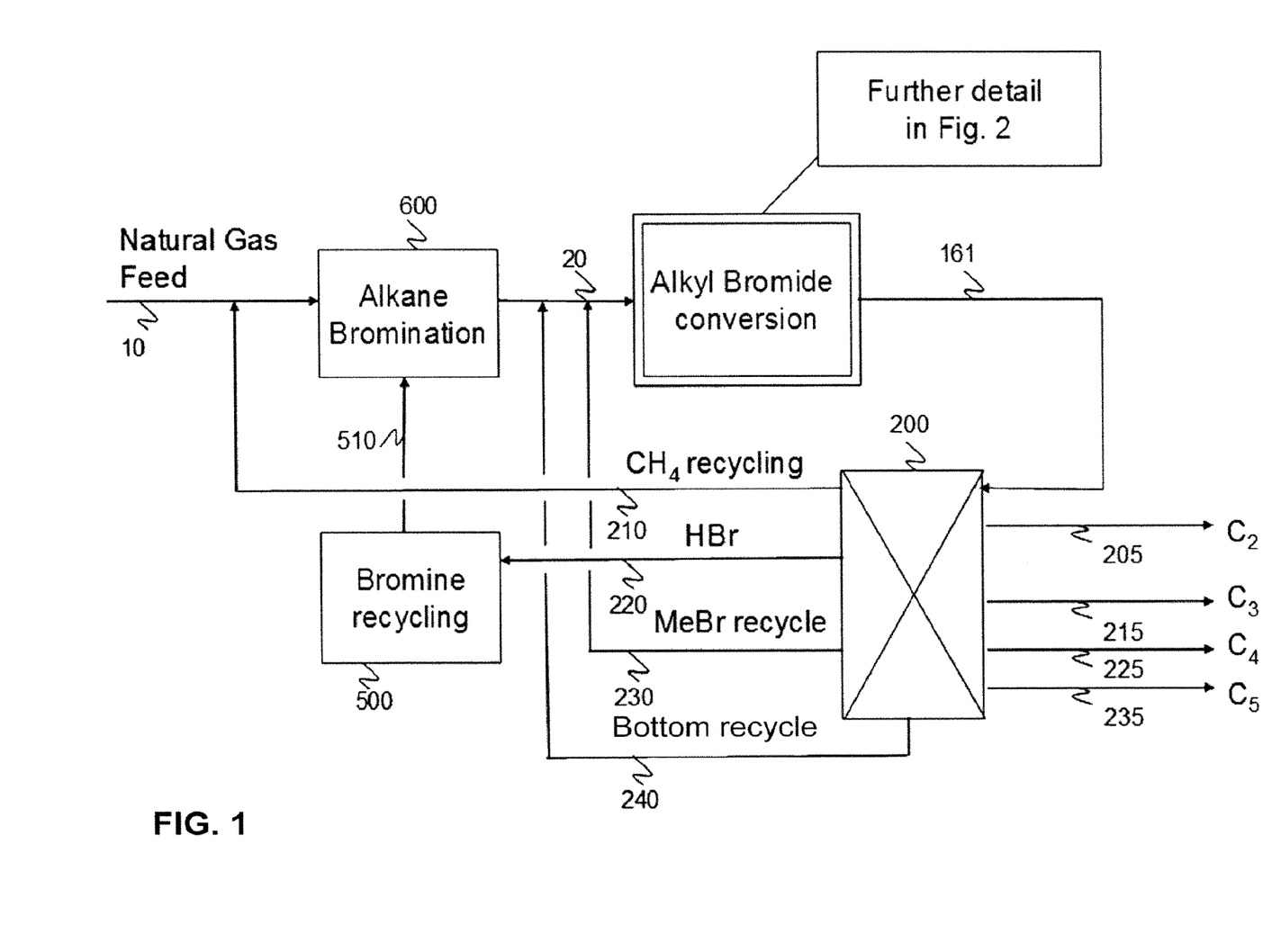
FIG. 1 is a schematic block flow diagram of a process for the production of saturated C2 to C5 hydrocarbons specifying the accurate location of an alkyl bromide conversion step of the present invention within the design of such halogen-based methane conversion processes.
Figure 2:
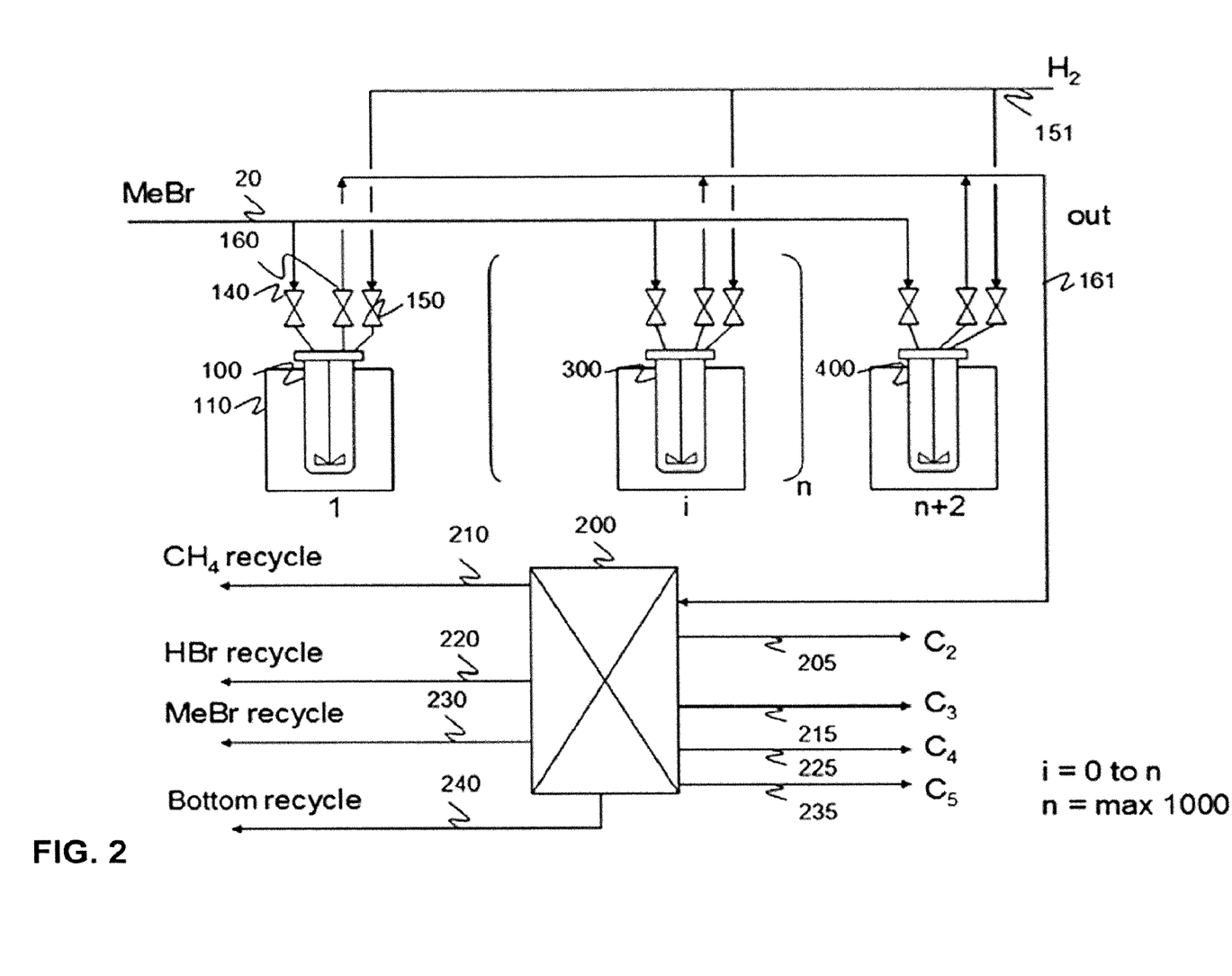
FIG. 2 is a schematic block flow diagram of the present invention detailing the reactor design for the conversion of methyl bromide.

Methyl Bromide Conversion:

A schematic block flow diagram generally depicting the process of the present invention is illustrated in FIG. 1 and a more detailed presentation of the alkyl bromide conversion is shown in FIG. 2.

Referring to FIG. 1 and FIG. 2, oxygen free natural gas 10 is mixed with the methane recycle stream 210 and fed into a first reaction vessel 600, where alkyl bromides, preferably methyl bromide, are produced. The product is mixed with the alkyl/methyl bromide recycle 230 as well as with the bottom recycle 240 and fed via line 20 into one or several high pressure autoclave(s) 100, (300, 400) (or other suitable equipment, such as a multistage reactor) with a heater 110 at ambient temperature. In the reactor(s) 100, (300, 400) where the methyl bromide 20 is pressurized and contacted with a catalyst, in particular a Lewis acid such as $AlBr_3$ and optionally other metals or metal derivatives, in particular metal salts, such as alkali metal salts, earth alkaline metal salts, in particular metal halides, all with no oxygen content. In this step the methyl bromide is converted into small hydrocarbons, HBr gas and carbon rich deposits.

If the deposition of carbon rich non-volatile compounds shall be prevented, hydrogen may be added to the alkyl halide conversion step in an amount of up to 40 mol % of fed methylbromide. As an alternative and preferred, a subsequent hydrogenation step may be added (see below). Such hydrogenation preferably is not performed to 100% but preferably a conversion of only 50 to 80% is aimed at, resulting in better selectivity towards C3 to C5 compounds which are the preferred products.

The temperature in such first part of the process is in the range of 100 to 300° C., in general in the range of 130° C. to 280° C., preferably in the range of 150 to 240° C., most preferred in the range of 160-180° C.

Reaction products, in gaseous form, are periodically withdrawn form reactor 100 at the outlet 160 from where they are transferred via line 161 into a separation unit 200 (for example a distillation column or an absorption column) and split into C1 (line 210) and higher hydrocarbons C2-C5 that can be retrieved together, or, preferably, separated into ethane, propane, propene, butane, isobutane, butene, isobu(ene, pentane and its isomers (indicated as lines 205, 215, 225, 235), HBr (line 220), methyl bromide (line 230) and bottom product (line 240). The methane, the HBr, the methyl bromide and the bottom product can be and preferably are recycled as follows:

Methane is recycled to the methyl bromide manufacturing unit 600 via line 210, HBr is fed back to the bromine generator 500 via line 220 where it is recycled to bromine and hydrogen, e.g. as detailed by GB1088441, GB11211781, U.S. Pat. No. 3,451,776 or JP52095594, and the bromine is reintroduced via line 510 to the bromination step 600.

Methyl bromide is recycled back to the methyl bromide stream 20.

The catalyst is regenerated by introducing hydrogen via line 151 into the high pressure autoclave(s) 100, (300, 400) forming small hydrocarbons ranging from methane to pentane, which are separated by distillation or adsorption in column 200.

The product hydrocarbons—if of undesired length or type (e.g. olefinic in stead of saturated)—may either be recycled into the reactor or used for further processing to polyethylene, olefins, waxes, gasoline and other fuels, polypropylene, etc.

Carbon formed during the conversion of methyl bromide deposits within reactor 100, in general on the bottom, on walls or inserts 140, 150 and remains thoroughly mixed with the transition metal bromide and/or Lewis acid comprising catalyst, preferably a Lewis acid with optionally other metals or metal derivatives, such as non-oxide metal salts, preferably alkali metal salts and/or earth alkaline metal salts, in particular halides, and/or transition metal bromides. The absence of any oxygen prevents the formation of any water, hence, HBr remains extremely dry. Corrosion as a partially ionic process is favored by the presence of minute amounts of water or oxides. With the exclusion of such oxides, water and/or oxygen even at very low concentrations of below 10 ppm allow an improved long-term handling of production equipment and catalysts. Reactor 100 is switched off of the methyl bromide feed line 20 once the rate of methyl bromide conversion drops below an acceptable value due to excessive carbon deposition in the reactor. Other parallel reactors to reactor 100 are used in the same way and may be switched off the methyl bromide feed for regeneration.

The temperature at which such methyl bromide conversion is carried out is an important and critical parameter determining the relative content of products in the stream. In general, higher temperature favor the formation of methane and carbon while under optimal conditions most of the methyl bromide is converted to hydrocarbons of 3-5 C per molecule and, inherently, some carbon deposits as suggested by the corresponding chemical equations:

$$3MeBr = 3HBr + C_2H_6 + C_{solid} \quad \text{(eqn 2)}$$

$$4MeBr = 4HBr + C_3H_8 + C_{solid} \quad \text{(eqn 3)}$$

$$5MeBr = 5HBr + C_4H_{10} + C_{solid} \quad \text{(eqn 4)}$$

$$6MeBr = 6HBr + C_5H_{12} + C_{solid} \quad \text{(eqn 5)}$$

Figure 5:
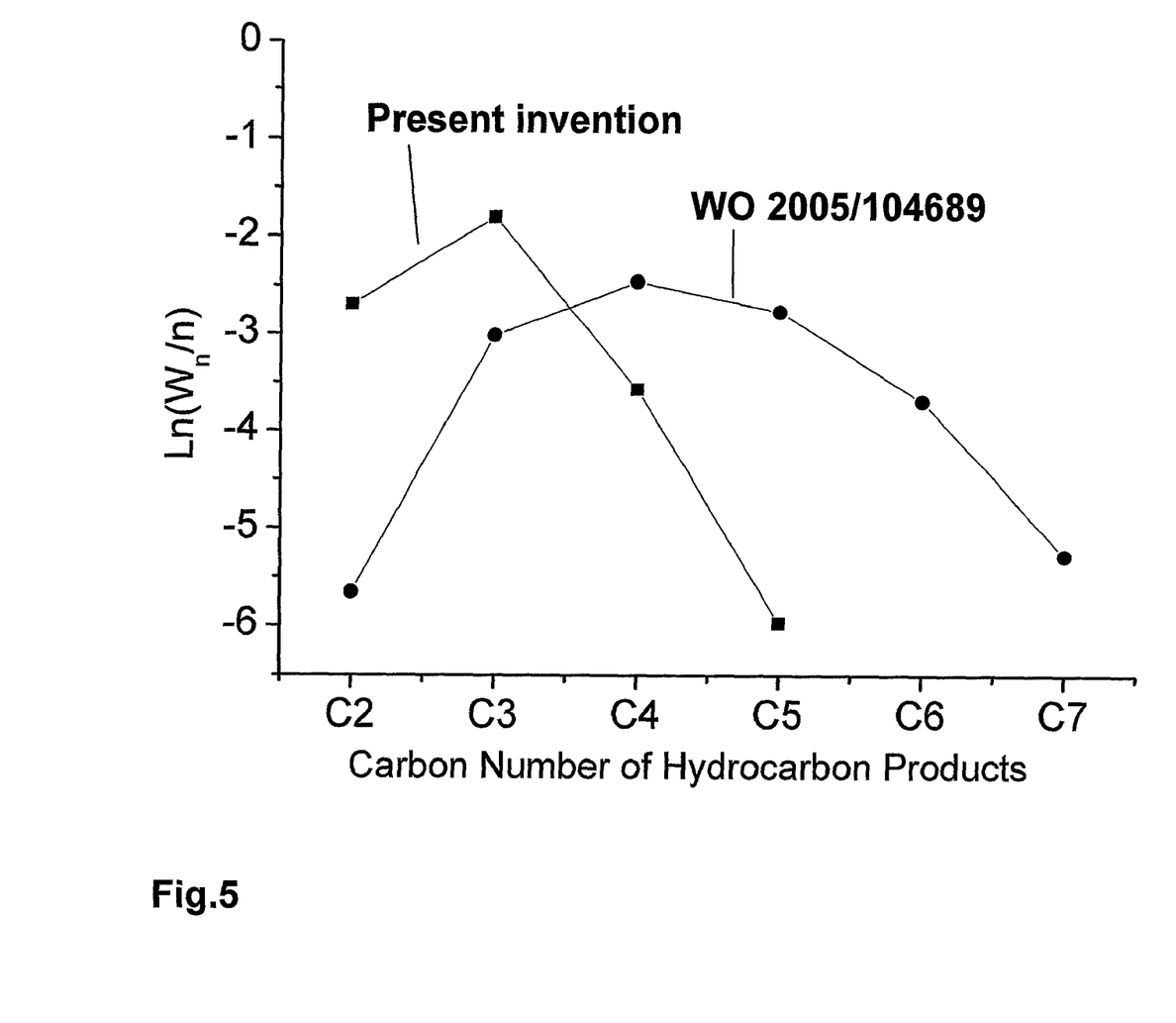
FIG. 5 is a Flory plot comparing the present invention and earlier patent application WO 2005/104689

The product distributions found with the present process stay in clear contrast to hydrocarbon distributions obtainable from the process disclosed in PCT/US2005/012655 (WO 2005/104689) as shown in the Flory plot in FIG. 5 where at above 300° C. light hydrocarbons were found and lower temperature was found to promote the formation of heavier hydrocarbons. No significant amounts of higher hydrocarbons are obtained in the course of the present invention. Interestingly, the process as outlined in PCT/US2005/012655 must also follow the stoichiometric equations as detailed above (eqn 2 to eqn 5) but the specification of WO 2005/104689 does not list significant carbon deposition. While the authors describe the burning and consecutive removal of such carbon deposits, the above stoichiometry clearly proofs that large losses of carbon result form such a process. Or, more quantitatively, if mainly manufacturing propane, about 25% of all carbon deposit within the reactor and on the zeolites (see eqn 3). These about 25% carbon are lost during regeneration if such carbon is oxidized.

Alternatively such carbon deposits might be reduced if products are chosen to contain significant amounts of aromatics since aromatics contain less hydrogen. Since bromide always leaves the reaction in the form of HBr, the inherent content of hydrogen in methyl bromide is 2 H per C. Hence, if a product contains more than 2 H per C in the mean, the stoichiometry as shown in the above equations dictates the deposition of carbon or a carbon rich product in the reactor. The present invention directly deals with this issue of stoichiometry by providing a way to elegantly convert such carbon deposits using the same catalysts and very similar temperature into similar products as during the conversion of methyl bromide.

Conversions generally achievable range between 50 to 97% of methyl bromide in a single run and underline the high suitability of the here-described process with respect to energy requirements since few or no methyl bromide has to be recycled. No significant formation of aromatics was observed which again stays in contrast to PCT/US2005/012655 where higher hydrocarbon fractions (e.g. C7) are mainly composed of substituted aromatics. At higher conversions of methyl bromide the inventors of PCT/US2005/012655 observed the undesired formation of methane. The inventors of said patent application further state that surprisingly, very little ethane or C2, C3 olefin components are formed. Full conversion was found at temperatures approaching 450° C. and an optimal temperature range was stated as 300° C. to 400° C. Full conversion in the present invention is achievable at temperatures below 260° C., preferably below 240° C.

Regeneration and Conversion of Carbon Rich Substances into C2 to C5 Hydrocarbons:

In a typical regeneration step, the deposited carbon is also converted into product hydrocarbons similar to the ones obtained form methyl bromide conversion by exposing the reactor contents (carbon, catalyst, in particular the Lewis acid, and optionally other metals or metal derivatives, such as non-oxide metal salts, preferably alkali metal salts and/or earth alkaline metal salts, in particular halides, and/or transition metal bromides) to pressurized hydrogen (pressure in the range of 10 to 150 bar) at temperatures between 100 to 300° C., optimally to temperatures between 220 to 280° C. The carbon can thereby be removed almost quantitatively and the reactivity of the catalyst or catalytic mixture is fully restored, thus making the corresponding reactor ready for a next methyl bromide conversion run. PCT/US2005/012655 describes a regeneration of the therein used oxide-based zeolite by periodically oxidizing carbon deposits at about 400 to 650° C. by addition of oxygen or air. Carbon deposits are then burned and not converted into desired products as described in the present invention. The removal by oxidation leads to a significant loss of carbon, or, in other words, methane, in particular if C2 to C5 hydrocarbons are the products of interest and not aromatics. The processes and regenerations of the state of the art methods include losses of 5 to 20% of carbon by oxidation. By contrast, the methods of the present invention include single pass conversions of methyl bromide combined with or followed by carbon hydrogenation of the deposits resulting in combined molar yields of carbon converted into small hydrocarbons (C2 to C5 range) exceeding 65%. Under preferred conditions the combined molar yields of carbon converted exceed 75% and under optimal conditions the obtainable yields are about 80% or more. No carbon is lost in the form of CO or $CO_2$ by catalyst regeneration. Hence, the present invention is especially well suited for large scale manufacturing of small hydrocarbons starting from methyl bromide or methyl bromide rich starting materials.

Although full hydrogenation of carbon rich material might be envisaged, it proved to be advantageous to perform the hydrogenation only to an extent of 50 to 80% of the carbon referred to the total carbon content.

Typical Run Conditions:

In a typical methyl bromide conversion process, methyl bromide is converted over a Lewis acid such as $AlBr_3$, or—under reaction conditions—some $AlBr_3$ may also be converted to $HAlBr_4$ due to a reaction of the Lewis acid $AlBr_3$ with the corresponding Lewis base HBr. Typical reactor temperatures are 180 to 280° C. and typical pressures range from 10 to 300 bar. Conversions can be above 92% depending on the Lewis acid used, as well as the pressure and temperature conditions. Inherently, the stoichiometry (see eqn 2 to 5) of such reactions demands the production of carbon rich, non volatile deposits during conversion. These carbon rich deposits are not lost as in prior attempts but directly converted to product hydrocarbons through hydrogenation with the same catalyst and in the same reactor as used for the conversion of the methyl bromide (step 1). Therefore, the process requires no catalyst exchange or modification as to allow this regeneration step.

Representative runs are described below and give an illustration to the skilled reader on how the present invention may be realized. Alternatively, suitable carbon rich substances can be directly delivered into the hydrogenation step and converted into C2 to C5 hydrocarbons at yields exceeding 70% (step 2). If the yield of the methane conversion step 1 is included, above 95% of carbon can be and in general are converted to hydrocarbons.

Conversion of Carbon Rich Substances into C2 To C5 Hydrocarbons:

The method developed for the regeneration of the catalyst and the conversion of carbon rich deposits into C2 to C5 hydrocarbons can not only be applied to the deposits formed during the inventive hydrocarbon conversion but also for the conversion of other carbon rich low oxygen products. A low oxygen content of below 50 parts per million mass, preferably below 10 ppm, most preferred below 5 ppm, is important to ensure sufficient lifetime of the catalyst and acceptably low corrosion of the reactor.

In such a method—as in a typical regeneration step—the carbon is also converted into product hydrocarbons similar to the ones obtained from methyl bromide conversion. In such method, the reactor is charged with the carbonaceous material and with a Lewis acid comprising catalyst as described above. Then pressurized hydrogen (pressure in the range of 10 to 150 bar) is added and the reactor is heated to and kept at temperatures between 100 to 300° C., optimally to temperatures between 220 to 280° C. The carbon can thereby be converted almost quantitatively and the reactivity of the catalyst or catalytic mixture is fully retained if the oxygen content of the carbonaceous material is kept low, preferably below 50 parts per million mass. By this method a conversion of at least 80% of the carbonaceous material into C2 to C5 hydrocarbons can be achieved in one run.

A further suitable carbon source for this process, is e.g. the carbon formed during the hydrogen production by the solar thermal decomposition of natural gas.

Also with regard to this method it is preferred to perform the hydrogenation only to an extent of 50 to 80% of the carbon referred to the total carbon content.

EXAMPLES

Example 1

Methyl bromide (1 mol) was transferred into an autoclave made out of Hasteloy (volume 300 ml) with 0.5 g of aluminium metal (grains, mean diameter 0.2 mm), sealed and heated to temperatures ranging from 150 to 260° C. Prior to loading the autoclave, the setup was dried under vacuum (pressure below 1 mbar, liquid nitrogen trap in the line) at 250° C. for at least 12 hours. At the start of the reaction, aluminum first reacted exothermally with methyl bromide to form the active Lewis acid $AlBr_3$ which partially forms complexes with HBr or MeBr resulting in species like $H[AlBr4]$ or $Me[AlBr4]$. After activation, the evolution of the reactant composition was followed by subsequent removal of gas samples and analysis. Table 1 shows the product mixtures obtainable for different runs. High selectivity to propane can be achieved. The conversion of methyl bromide was executed several times in a row with catalyst regeneration between runs. Both the methyl bromide conversion and the regeneration steps yielded valuable product hydrocarbons. Detailed compositions are given in Table 1 (methyl bromide conversion) and Table 2 (regeneration steps)

TABLE 1

| | | $S_{product}$ | | | | | |
|---|---|---|---|---|---|---|---|
| Run | $X_{(CH3Br)}$ | Methane | Ethane | Propane | Iso-butane | Butane | Pentane |
| 1 | 54% | 6.04% | 5.68% | 59.15% | 15.10% | 11.37% | 2.84% |
| 2 | 56% | 8.78% | 7.06% | 60.50% | 11.83% | 9.54% | 2.29% |
| 3 | 44% | 10.16% | 6.87% | 57.14% | 13.46% | 9.07% | 3.30% |

Values are given as % carbon in the product gaseous mixture after reaction for conversions around 50%.

TABLE 2

| Run | time [min] | Methane | Ethane | Propane | Iso-butane | Butane |
|---|---|---|---|---|---|---|
| Regeneration 1 | 1320 | 23% | 33% | 30% | 8% | 5% |
| Regeneration 2 | 1260 | 30% | 45% | 21% | 3% | 2% |

Example 2

Using a setup and catalyst as described in Example 1, methyl bromide and an additional gas were fed together into the reactor. The addition of an inert gas (nitrogen) resulted in minor changes in the reaction rate or products obtained. Addition of hydrogen, however, promoted a strong increase in methane production on the expense of C2 to C5 hydrocarbons. This shows that the hydrogenation can run parallel to the methyl bromide conversion, that, however, a separated conversion of MeBr and regeneration by hydrogenation of carbon deposits, is preferred.

TABLE 3

| Run | MeBr[a] | $CH_4$[a] | $C_3H_8$[a] |
|---|---|---|---|
| Ref | 40 | 12 | 31 |
| +$H_2$ | 19 | 73 | 4 |
| +$N_2$ | 40 | 21 | 26 |

[a]content of carbon in the product gases.

All runs contained 0.5 g aluminum metal that was directly converted into the catalyst during the run.
MeBr used: 0.9-1.0 mol
$H_2$ used: 0.8-1 mol
$N_2$ used: 80 bar at ambient temperature ($N_2$ does not react)
Temperature: 210° C.
Pressure: 82 bar Example 3

Figure 3:
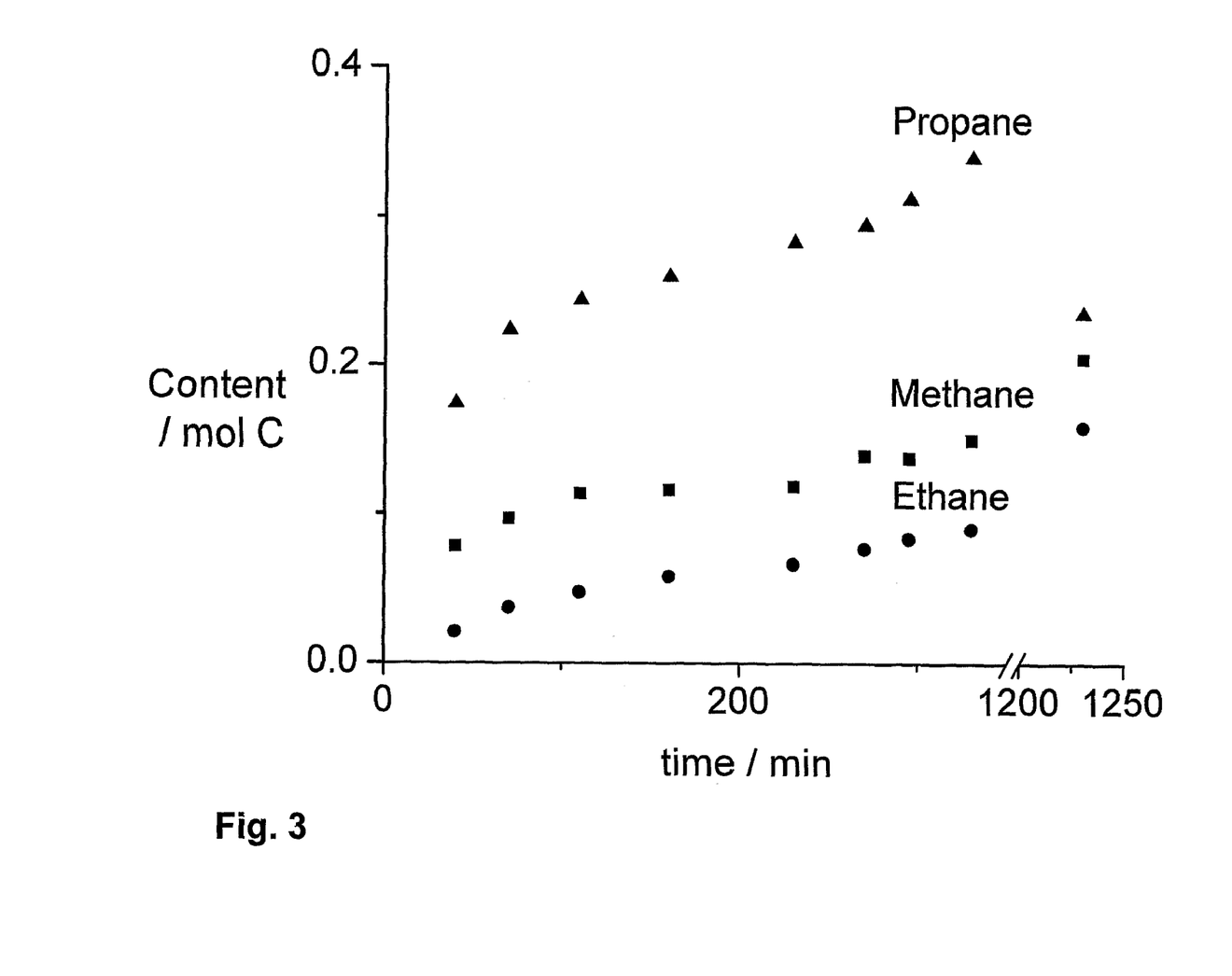
FIG. 3 is a graph showing the methyl bromide conversion vs. time of Example 3 performed with 55.6 mmol catalyst, leading to a final conversion of 92% of the methyl bromide.
Figure 4:
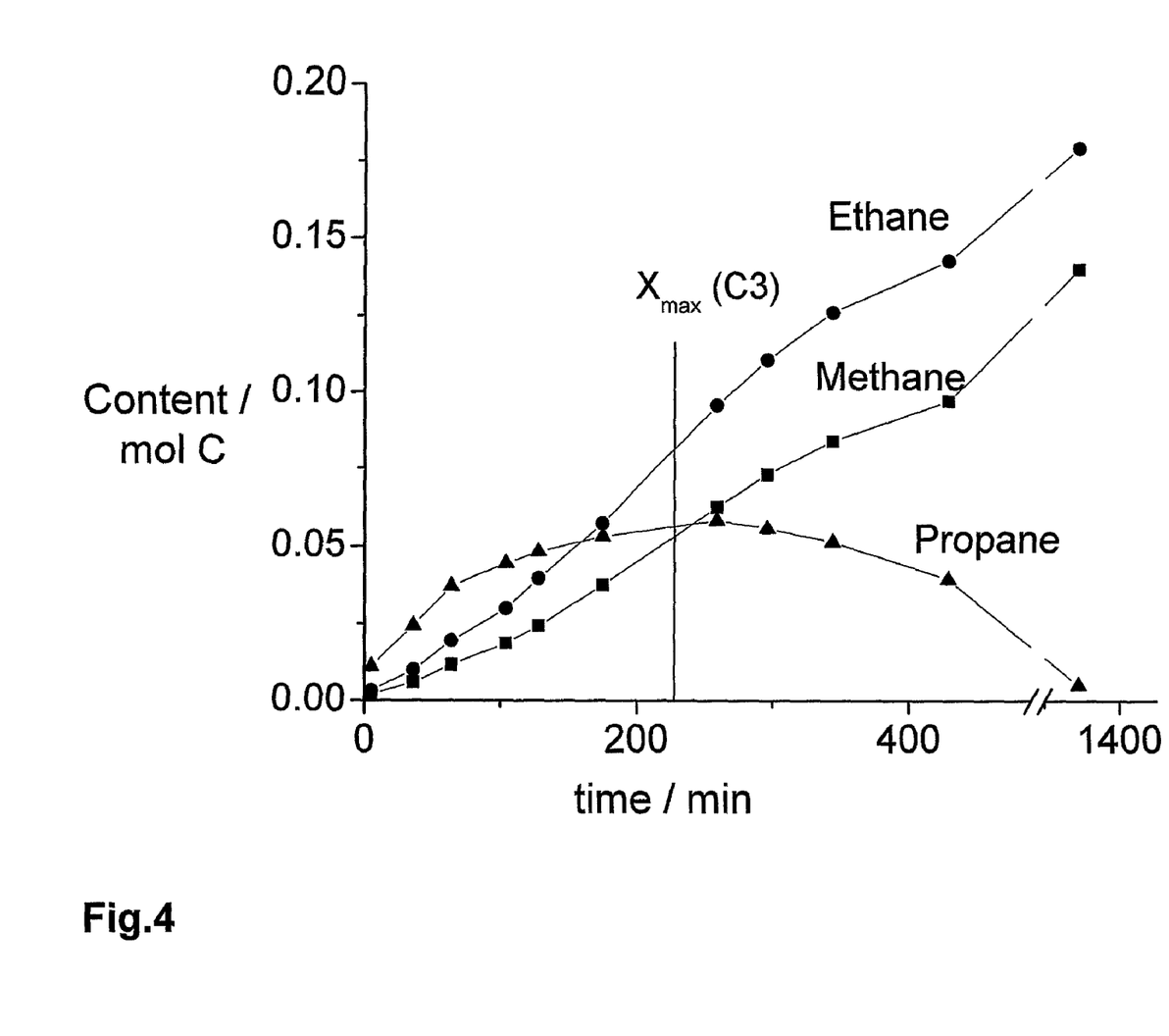
FIG. 4 is a graph showing the regeneration run as described in example 1. It indicates that propane is cracked to methane and ethane during the activation process.

This example was performed using a setup as described in Example 1 with 1.5 g aluminum metal, which was reacted to $AlBr_3$ in a first step. After activation, the evolution of the reactant composition was followed by subsequent removal of gas samples and analysis made by gas chromatography, either coupled to a mass spectrometer (GC-MS) or to a flame ionization detector (GC-FID). The results of the methyl bromide conversion reaction are given in FIG. 3. This Figure shows that higher conversion is not in favor of the production of C2-C5 alkanes. A regeneration run performed as described in Example 1 is shown in FIG. 4. This Figure indicates that propane is cracked to methane and ethane during the activation process. Thus, also the regeneration run should not be performed at total conversion rate but preferably at conversion rates of 50 to 80% of total carbon.

Example 4

The setup as described in example 1 was used with a catalyst containing 55 mmol AlBr3 and with an additional co-catalyst of 55 mmol LiBr. After feeding 1 mol methylbromide the reaction was heated to 180° C. The resulting product gas showed that the reaction with an alkali metal salt such as LiBr as a co-catalyst has a higher selectivity towards propane at high conversion rate:

TABLE 4

| | $S_{product}$ | | | | | |
|---|---|---|---|---|---|---|
| $X_{(CH3Br)}$ | Methane | Ethane | Propane | Isobutane | Butane | Pentane |
| 91% | 14% | 6% | 66% | 6% | 6% | 2% |

Values are given in % carbon in the product gaseous mixture after reaction for conversion of above 90% methyl bromide.

While there are shown and described presently preferred embodiments of the invention, it is to be distinctly understood that the invention is not limited thereto but may be otherwise variously embodied and practiced within the scope of the following claims.

REFERENCES

[1] Murray D. K., Howard T., Goguen P. W., Krawietz T. R., Haw J. F.; Methyl halide reactions on multifunctional metal-exchanged zeolite catalysts, *J. Am Chem. Soc* 116: 6354 (1994)
[2] White M. C., Douglas L. J., Hackett J. P. Anderson R. R.; Characterization of synthetic gasoline from the chloromethane-zeolite reaction, *Energy & Fuels* 6: 76 (1992)
[3] Lersch P., Bandermann F.; Conversion of chloromethane over metal-exchanged ZSM-5 to higher hydrocarbons, *Applied Catalysis* 75: 133 (1991)
[4] Noronha L. A., Souza-Aguiar E. F., Mota C. J. A.; Conversion of chloromethane to light olefins catalyzed by ZSM-5 zeolites, *Catalysis today* 101: 9 (2005)
[5] Sun Y., Campell S. M., Lunsford J. H., Lewis G. E., Plake D., Tau L.; The catalytic conversion of methyl chloride to ethylene and propylene over phosphorus-modified Mg-ZSM-5 zeolites, *Journal of catalysis* 143: 32 (1993)
[6] Lorkovic I. M., Yilmaz A., Yilmaz G. A., Zhou X., Laverman L. E., Sun S., Schaefer D. J., Weiss M., Noy M. L., Cutler C. I., Sherman J. H., McFarland E. W., Stucky G. D., Ford P. C.; A novel integrated process for the functionalization of methane and ethane: bromine as mediator, *Catalysis today* 98: 317 (2004)

[7] Zhou X. P., Yilmaz A., Yilmaz G. A., Lorkovic I. M., Laverman L. E., Weiss M., Sherman J. H., McFarland E. W., Stucky G. D., Ford P. C.; An integrated process for partial oxidation of alkanes, *Chem Comm* 2294 (2003)

[8] Lorkovic I. M., Noy M., Weiss M., Sherman J., McFarland E., Stucky G. D., Ford P. C.; C1 coupling via bromine activation and tandem catalytic condensation and neutralization over CaO/zeolite composites, *Chem Comm* 566 (2004)

[9] Sun S., Lorkovic I. M., Weiss M., Sherman J. H., Stucky G. D., Ford P. C., McFarland E. W.; A general integrated process for synthesizing olefin oxides, *Chem Comm* 2100 (2004)

[10] Yilmaz A., Zhou X., Lorkovic I. M., Yilmaz G. A., Laverman L., Weiss M., Sun S., Schaefer D., Sherman J. H., McFarland E. W., Ford P. C., Stucky G. D.; Bromine mediated partial oxidation of ethane over nanostructured zirconia supported metal oxide/bromide, *Microporous and Mesoporous Materials* 79: 205 (2005)

[11] Degirmeneci V., Uner D., Yilmaz A.; Methane to higher hydrocarbons via halogenation, *Catalysis today* 106: 252 (2005)

[12] Smudde G. H., Bailey W. I., Felker B. S., Langan G., Langan M. A.; Materials selection for HBr service, *Corrosion science* 37: 1931 (1995)

[13] Olah G. A., Renner R., Schillin P., Mo Y. K.; Electrophilic reactions at single bonds 0.17. $SBF_5$, $AlCl_3$, and $AgSBF_6$ catalyzed chlorination and chlorolysis of alkanes and cycloalkanes, *J. Am. Chem. Soc.* 95: 7686 (1973)

[43] Sokol A. A., Catlow C. R. A., Garcés J. M., Kuperman A.; Computational Investigation into the Origins of Lewis Acidity in Zeolites, *Advanced Materials* 12, No. 23: 1801 (2000)

The invention claimed is:

1. A process for the production of saturated hydrocarbons with 2 to 5 carbon atoms per molecule by conversion of methyl halides or methyl halide rich materials, wherein the methyl halide is reacted over a catalyst comprised of a transition metal bromide and/or Lewis acid under the exclusion of oxygen in any form exceeding a level of at most 5 parts per million mass based on the combined mass of methyl halide or methyl halide rich materials and catalyst.

2. The method of claim 1, wherein the catalyst comprises a Lewis acid.

3. The method of claim 1, wherein the methyl halide is methyl bromide or a methyl bromide rich material.

4. The method of claim 3 wherein the methyl bromide content of the methyl bromide rich material is at least 50%, by volume.

5. The method of claim 1 wherein the conversion is performed at temperatures in the range of 100 to 300° C.

6. The method of claim 1 wherein the conversion is performed at pressures from 10 to 300 bars.

7. The method of claim 1, wherein the catalyst further comprises a metal and/or an oxygen free metal derivative, said metal derivative being selected from alkali metal salts and/or earth alkaline metal salts.

8. The method of claim 1 wherein the catalyst consists of a Lewis acid.

9. The method of claim 8 wherein the Lewis acid is $AlBr_3$, optionally together with LiBr.

10. The method of claim 1, wherein the reaction is performed in the presence of hydrogen.

11. The method of claim 1, wherein the hydrocarbons formed in the conversion step are removed and separated into C2 to C5 hydrocarbons, methane, methyl bromide, HBr and C6 and higher hydrocarbons.

12. The method of claim 11, wherein the C2 to C5 hydrocarbons are separated into ethane, propane, propene, butane, isobutane, butene, isobutene, pentane and its isomers.

13. The method of claim 11, wherein the methane, the methyl bromide, the HBr and optionally the C6 or higher hydrocarbons are recycled into the hydrocarbon conversion reaction.

14. The method of claim 1, wherein carbon rich deposits formed in the reactor and/or on the catalyst during methyl halide conversion are removed in a separate regeneration step but in the same catalyst comprising reactor and without any solids transported or any catalyst added, said separate regeneration step comprising the application of hydrogen to said reactor at a pressure from 40 to 150 bars and a temperature between 100 to 300° C.

15. The method of claim 14, wherein the conversion of the methyl halide is performed in the simultaneous presence of hydrogen.

16. The method of claim 14, wherein the hydrocarbons are removed and separated into methane, C2 to C5, C6 and higher hydrocarbons, methyl bromide and HBr.

17. The method of claim 16, wherein at least one of methane, C6 and higher hydrocarbons, methyl bromide and HBr are recycled.

18. The method of claim 16, wherein methane, C6 and higher hydrocarbons, methyl bromide and HBr are recycled.

* * * * *